US012685655B2

(12) United States Patent
Curran et al.

(10) Patent No.: US 12,685,655 B2
(45) Date of Patent: Jul. 21, 2026

(54) DEVICES, SYSTEMS, AND METHODS FOR OCCLUDING AN ANATOMICAL PASSAGE

(71) Applicant: BOSTON SCIENTIFIC SCIMED, INC., Maple Grove, MN (US)

(72) Inventors: Darren Gerard Curran, Galway (IE); David Collins, Galway (IE); Paul E. Tierney, Galway (IE); Brian Pierce Bolger, Kilkenny (IE); John O'Driscoll, Galway (IE); Douglas Melanson, Natick, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 503 days.

(21) Appl. No.: 18/106,861

(22) Filed: Feb. 7, 2023

(65) Prior Publication Data

US 2023/0248561 A1      Aug. 10, 2023

Related U.S. Application Data

(60) Provisional application No. 63/307,764, filed on Feb. 8, 2022.

(51) Int. Cl.
*A61F 5/00*          (2006.01)
(52) U.S. Cl.
CPC .................................. *A61F 5/0079* (2013.01)
(58) Field of Classification Search
CPC .................................. A61F 5/0079; A61F 2/04
See application file for complete search history.

(56) References Cited

U.S. PATENT DOCUMENTS

| | | | |
|---|---|---|---|
| 9,730,822 B2 | 8/2017 | O'Neill et al. | |
| 9,744,062 B2 | 8/2017 | O'Neill et al. | |
| 9,913,744 B2 | 3/2018 | O'Neill et al. | |
| 11,020,215 B2 | 6/2021 | Donadio, III et al. | |
| 2004/0210281 A1* | 10/2004 | Dzeng ..................... | A61F 7/123 607/96 |
| 2008/0109087 A1 | 5/2008 | Durgin | |

(Continued)

FOREIGN PATENT DOCUMENTS

| | | |
|---|---|---|
| DE | 202020005650 U1 | 6/2022 |
| EP | 1555970 A1 | 7/2005 |

OTHER PUBLICATIONS

Invitation to Pay Additional Fees mailed May 4, 2023 for International Application No. PCT/US2023/012522.

*Primary Examiner* — Ariana Zimbouski
(74) *Attorney, Agent, or Firm* — Seager, Tufte & Wickhem, LLP

(57)          ABSTRACT

An occlusion device having a lumen defined therethrough and a saddle narrower than saddles of prior occlusion devices or stents to allow provision of an occlusion element with respect to a portion of the saddle to occlude flow of materials through the saddle. The inner diameter of the narrowed saddle may be 6 mm or less. The occlusion element may be formed from a material which plugs a portion of the occlusion device lumen extending through the saddle and/or which restrains a portion of the saddle from expanding thereby occluding flow of materials therethrough. The remainder of the saddle and/or inwardly facing surfaces of at least one retention member extending outwardly along an end of the saddle may be configured to promote tissue ingrowth, such as by remaining uncoated.

20 Claims, 3 Drawing Sheets

(56)            References Cited

U.S. PATENT DOCUMENTS

| | | | |
|---|---|---|---|
| 2017/0333240 A1* | 11/2017 | Stangenes | A61B 17/00234 |
| 2018/0250118 A1* | 9/2018 | Folan | A61F 2/04 |
| 2019/0125558 A1* | 5/2019 | Coyne | A61F 2/2412 |
| 2019/0298559 A1* | 10/2019 | Gupta | A61B 17/1114 |
| 2020/0268537 A1 | 8/2020 | Reisin et al. | |
| 2021/0196283 A1 | 7/2021 | Zhang et al. | |
| 2021/0244523 A1 | 8/2021 | Gupta et al. | |

* cited by examiner

DEVICES, SYSTEMS, AND METHODS FOR OCCLUDING AN ANATOMICAL PASSAGE

CROSS-REFERENCE TO RELATED APPLICATIONS

This application claims the benefit of priority of U.S. Provisional Application No. 63/307,764, filed Feb. 8, 2022, the entire disclosure of which is hereby incorporated by reference herein for all purposes.

FIELD

The present disclosure relates generally to the field of implantable devices, systems, and methods. More particularly, the present disclosure relates to the field of implantable devices, systems, and methods for occluding an anatomical passage.

BACKGROUND

Various medical treatments involve occluding flow of materials through a body passage. For instance, treatment methods for various medical conditions, such as obesity, diabetes, or duodenal ulcers, involve bypassing the duodenum or restricting flow of materials through the duodenum. Common bariatric procedures include Sleeve Gastrectomy, Roux-en-Y Gastric Bypass and Gastric Banding, and are either obstructive (as in Gastric Banding and Sleeve Gastrectomy), or malabsorptive or both (as with Roux-en-Y). All of these procedures are highly invasive with the associated possibility of serious complications. A newer, less invasive procedure, with less associated trauma and lower risk for complication, involves creation of an anastomosis, such as between the stomach and the jejunum (a gastrojejunostomy, or GJ for short), and a pyloric closure via an endoscopic procedure (e.g., endoscopic ultrasound procedure, or EUS for short), such as a NOTES (natural orifice transluminal endoscopic surgery) procedure. If the treatment requires complete bypass of the duodenum, then occlusion (e.g., full occlusion) of the pylorus may be indicated. An occlusion device, such as a duodenal exclusion device, may be placed in the pyloric sphincter to inhibit or block passage of materials (fluid, chyme, etc.) from the stomach through the pylorus and into the duodenum. Various challenges to preventing migration of a deployed occlusion device are presented by the natural movements of the body (e.g., the gastrointestinal system) as well as the constant flow of materials against the occlusion device. Peristaltic movement of the pylorus to pass materials therethrough (e.g., distally into the small intestine), generally less frequent reverse peristalsis through the pylorus (proximally into the stomach), as well as the natural tendency of the pylorus to eject materials therein present particular challenges for placement and retention of pyloric occlusion devices. Backpressure from the large and small intestines, via the duodenum, also may cause migration of the device. Accordingly, improved devices, systems, and methods for occluding flow of materials within a body, while also resisting migration of an occlusion device with respect to the site at which it is deployed, would be welcome.

SUMMARY

This summary of the disclosure is given to aid understanding, and one of skill in the art will understand that each of the various aspects and features of the disclosure may advantageously be used separately in some instances, or in combination with other aspects and features of the disclosure in other instances. No limitation as to the scope of the claimed subject matter is intended by either the inclusion or non-inclusion of elements, components, or the like in this summary.

In accordance with various principles of the present disclosure, an occlusion device has a first end, a second end, and an intermediate region therebetween, and defining a lumen therethrough; a radially outwardly extending first retention member along the first end of the occlusion device; a radially outwardly extending second retention member along the second end of the occlusion device; a saddle along the intermediate region of the occlusion device, and an occlusion element positioned along at least a portion of the saddle to occlude flow of materials through the lumen; where the occlusion element is formed of a coating material.

In some embodiments, at least one of the viscosity, solids percent, thickness, durometer, or flexibility of the coating material is selected to allow the coating material to plug at least a portion of the lumen through the occlusion device. In some embodiments, the coating material fills the portion of the lumen to define an inner diameter of less than 2 mm through the portion of the lumen. In some embodiments, the coating material extends only about 2-3 mm along the saddle. In some embodiments, the coating material is limited to a central region of the saddle with surrounding regions of the saddle uncoated to promote tissue ingrowth.

In some embodiments, at least one of the viscosity, solids percent, thickness, durometer, or flexibility of the coating material is selected to allow the coating material to restrain at least a portion of the saddle from expanding, thereby occluding flow of material through the lumen defined through the occlusion device.

In some embodiments, the outer diameter of at least one of the first retention member or the second retention member is at least about ten times greater than an outer diameter of the saddle.

In some embodiments, the first retention member and the second retention member have surfaces facing the saddle which are configured to promote tissue ingrowth therein.

In accordance with various principles of the present disclosure, a method of occluding the lumen of an occlusion device includes narrowing an intermediate region of a tubular element to define a saddle; forming a first retention member with an outer diameter larger than the outer diameter of the saddle along a first end of the tubular element; forming a second retention member with an outer diameter larger than the outer diameter of the saddle along a second end of the tubular element; and applying a coating material to a portion of the saddle region to occlude the portion of the occlusion device lumen extending therein.

In some aspects, the method further includes constraining a portion of the saddle so that the diameter of the lumen within the constrained portion of the saddle is 6 mm or less.

In some aspects, applying a coating further comprises applying a coating material with at least one of a viscosity, solids percent, thickness, durometer, or flexibility allowing the coating material to plug at least a portion of the lumen through the occlusion device and/or to restrain the coated portion of the saddle from expanding to thereby occlude flow of material through the lumen defined through said occlusion device.

In some aspects, the method further comprises leaving a portion of the saddle, and the surfaces of the first retention member and the second retention member facing the saddle uncoated to promote tissue ingrowth therein.

In accordance with various principles of the present disclosure, an occlusion device has a first end, a second end, and an intermediate region therebetween, and defining a lumen therethrough; a radially outwardly extending first retention member along the first end of the occlusion device; a radially outwardly extending second retention member along the second end of the occlusion device; a saddle along the intermediate region of the occlusion device; and an occlusion element positioned along at least a portion of the saddle to occlude flow of materials through the lumen; where the diameter of at least a portion of the lumen extending through the saddle is less than about 6 mm.

In some embodiments, the occlusion element is formed from a coating material applied to the saddle. In some embodiments, the occlusion element is positioned about a portion of the exterior of the saddle to restrict expansion of the saddle. In some embodiments, the occlusion element extends within a portion of the lumen extending through the saddle to form a plug within a portion of the lumen extending through the saddle. In some embodiments, the coating material is limited to a central region of the saddle with surrounding regions of the saddle uncoated to promote tissue ingrowth. In some embodiments, surfaces of the first retention member and the second retention member facing the saddle are uncoated to promote tissue ingrowth therein In some embodiments, the outer diameter of at least one of the first retention member or the second retention member is at least about ten times greater than an outer diameter of the saddle.

In some embodiments, the diameter of at least a portion of the lumen extending through the saddle is about 2 mm.

In accordance with various principles of the present disclosure, a method of occluding a body passage includes deploying, within the body passage, an occlusion device defining a lumen therethrough and having a saddle region, a first retention member extending outwardly along a first end of the occlusion device, and a second retention member extending outwardly along a second end of the occlusion device; where: an occlusion element is provided along a portion of the saddle to occlude the portion of the occlusion device lumen therein, and a remaining portion of the saddle not occluded by the occlusion element is uncoated to promote tissue ingrowth therein.

In some aspects, the occlusion element is a coating plugging the portion of the occlusion device lumen within the portion of the saddle along which the occlusion element is provided.

In some aspects, the occlusion element prevents expansion of the portion of the saddle along which the occlusion element is provided.

In some aspects, surfaces of the first retention member and the second retention member configured to be seated against tissue are configured to promote tissue ingrowth therein.

In some aspects, at least the portion of the saddle along which the occlusion element is provided has an inner diameter of 6 mm or less Implementations of a device formed in accordance with various principles of the present disclosure may include one or more of the following features separately and independently, or in any appropriate combination: The device may include an occlusion element plugging and/or configured to prevent expansion of the portion of the occlusion device lumen within the portion of the saddle along which the occlusion element is provided. At least the portion of the saddle along which the occlusion element is provided may have an inner diameter of 6 mm or less. The occlusion element may extend within a portion of the lumen extending through the saddle. The occlusion element may be positioned about a portion of the exterior of the saddle to restrict expansion of the saddle. The occlusion element may be formed from a coating material applied to the saddle. The coating material may fill the portion of the lumen to define an inner diameter of less than 2 mm through the portion of the lumen. The coating material may extend only about 2-3 mm along the saddle. The coating material may be limited to a central region of the saddle with surrounding regions of the saddle uncoated to promote tissue ingrowth. At least one of the viscosity, solids percent, thickness, durometer, or flexibility of the coating material may be selected to allow the coating material to plug at least a portion of the lumen through the occlusion device. At least one of the viscosity, solids percent, thickness, durometer, or flexibility of the coating material may be selected to allow the coating material to restrain at least a portion of the saddle from expanding, thereby occluding flow of material through the lumen defined through the occlusion device. The outer diameter of at least one of the first retention member or the second retention member may be at least about ten times greater than an outer diameter of the saddle. The first retention member and the second retention member may have surfaces facing the saddle which are configured to promote tissue ingrowth therein. Surfaces of the first retention member and the second retention member facing the saddle may be configured to promote tissue ingrowth therein. The diameter of at least a portion of the lumen extending through the saddle may be about 2 mm. The device may be formed by constraining a portion of the saddle so that the diameter of the lumen within the constrained portion of the saddle is 6 mm or less. The device may be formed by applying a coating material with at least one of a viscosity, solids percent, thickness, durometer, or flexibility allowing the coating material to plug at least a portion of the lumen through the occlusion device and/or to restrain the coated portion of the saddle from expanding to thereby occlude flow of material through the lumen defined through the occlusion device. A portion of the saddle, and/or surfaces of the first retention member and the second retention member facing the saddle and configured to be seated against tissue may be configured to promote tissue ingrowth therein.

These and other features and advantages of the present disclosure, will be readily apparent from the following detailed description, the scope of the claimed invention being set out in the appended claims. While the following disclosure is presented in terms of aspects or embodiments, it should be appreciated that individual aspects can be claimed separately or in combination with aspects and features of that embodiment or any other embodiment.

BRIEF DESCRIPTION OF THE DRAWINGS

Non-limiting embodiments of the present disclosure are described by way of example with reference to the accompanying drawings, which are schematic and not intended to be drawn to scale. The accompanying drawings are provided for purposes of illustration only, and the dimensions, positions, order, and relative sizes reflected in the figures in the drawings may vary. For example, devices may be enlarged so that detail is discernable, but is intended to be scaled down in relation to, e.g., fit within a working channel of a delivery catheter or endoscope. In the figures, identical or nearly identical or equivalent elements are typically represented by the same reference characters, and similar ele-

5

Figure 1:
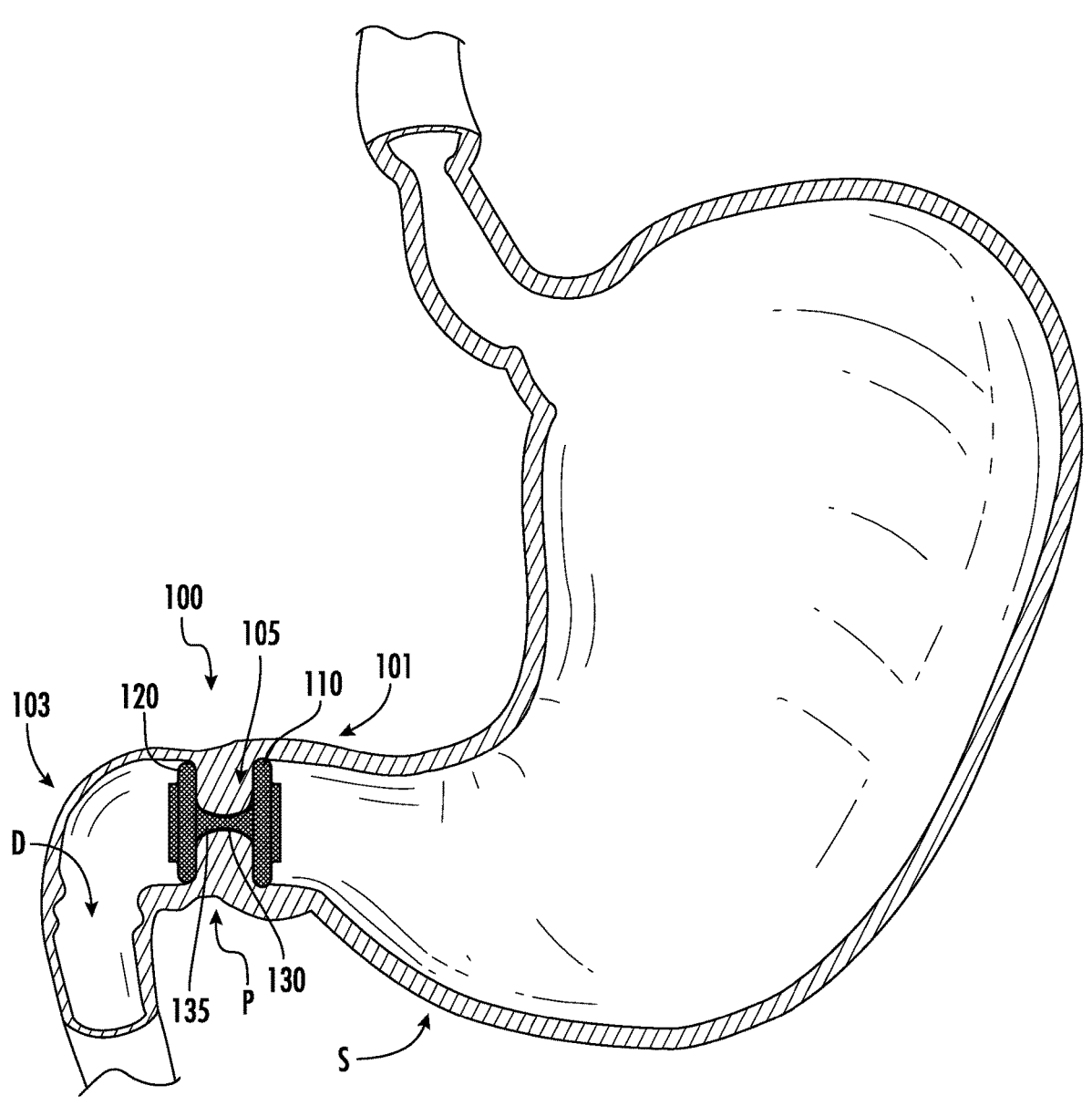

6 ments are typically designated with similar reference numbers differing in increments of 100, with redundant description omitted. For purposes of clarity and simplicity, not every element is labeled in every figure, nor is every element of each embodiment shown where illustration is not necessary to allow those of ordinary skill in the art to understand the disclosure.

The detailed description will be better understood in conjunction with the accompanying drawings, wherein like reference characters represent like elements, as follows:

FIG. 1 illustrates a perspective view of an embodiment of an occlusion device formed in accordance with various aspects of the present disclosure and positioned in a schematic representation of a gastrointestinal environment.

Figure 2:
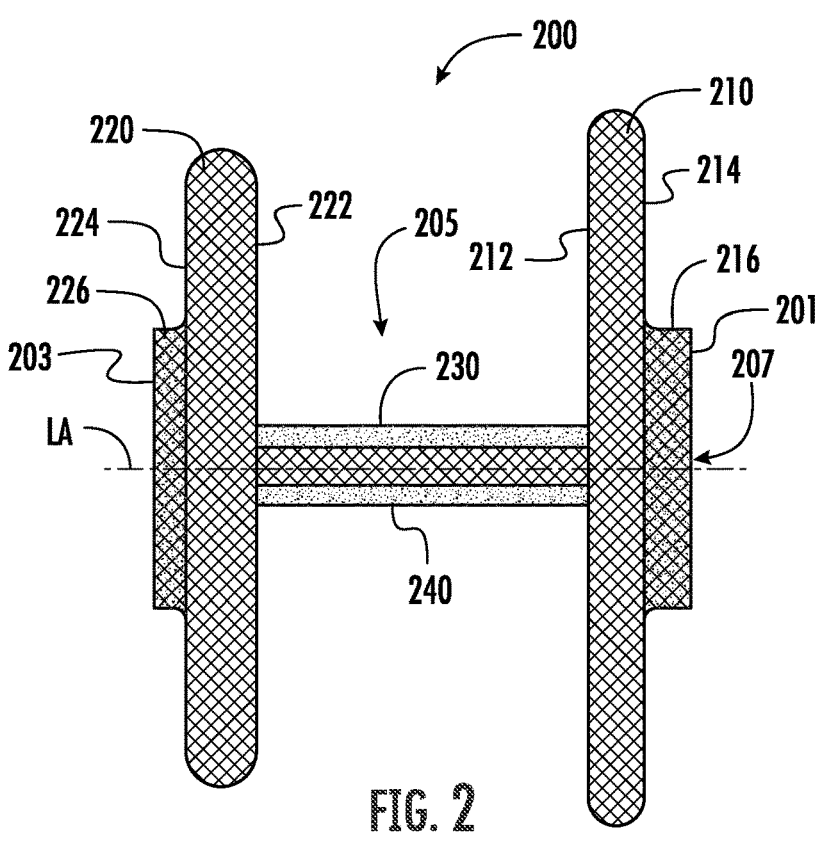

FIG. 2 illustrates an elevational view of an example of an embodiment of an occlusion device formed in accordance with various principles of the present disclosure.

Figure 3:
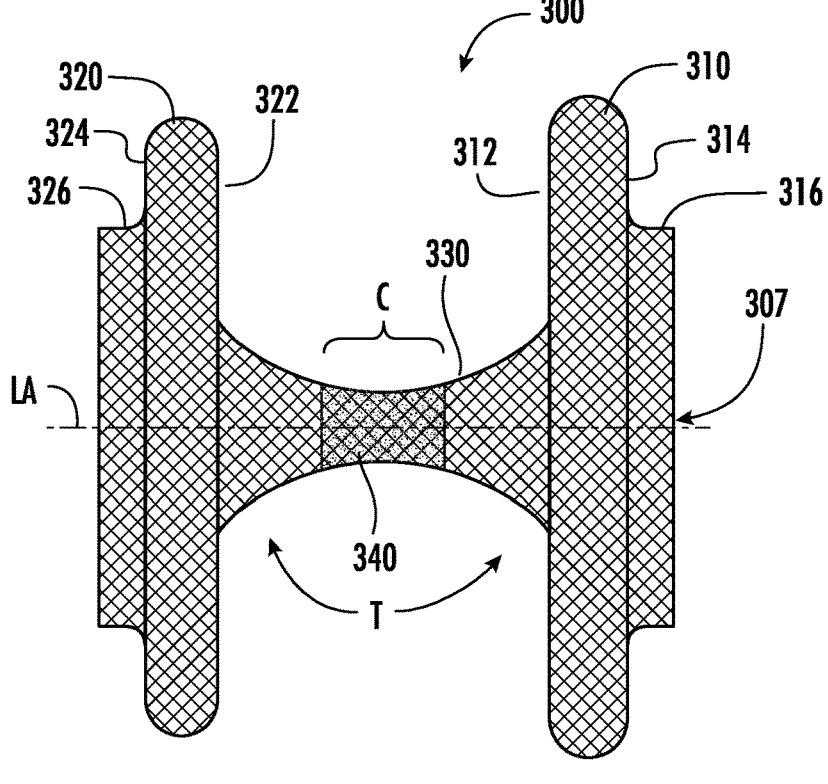

FIG. 3 illustrates an elevational view of another example of an embodiment of an occlusion device formed in accordance with various principles of the present disclosure.

Figure 4:
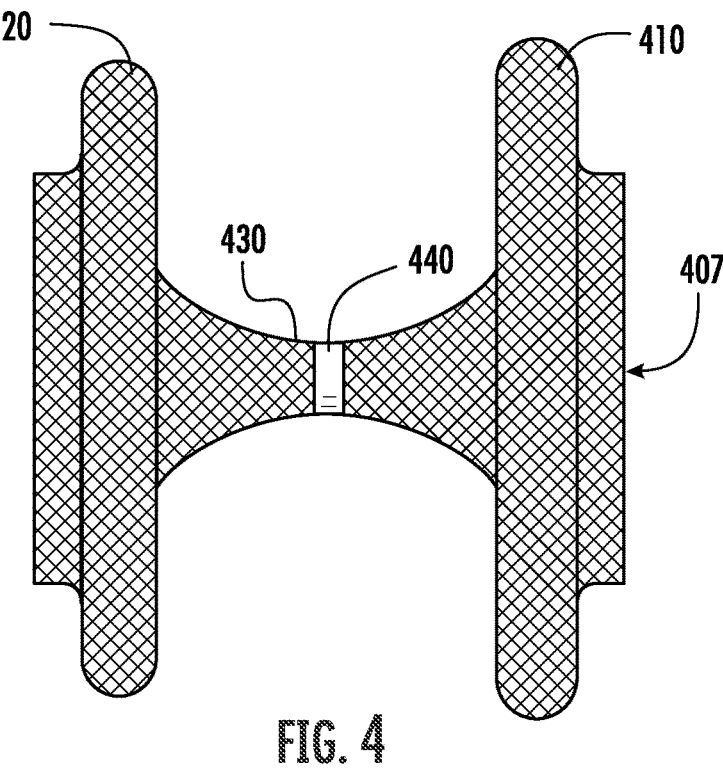

FIG. 4 illustrates an elevational view of another example of an embodiment of an occlusion device formed in accordance with various principles of the present disclosure.

Figure 5:
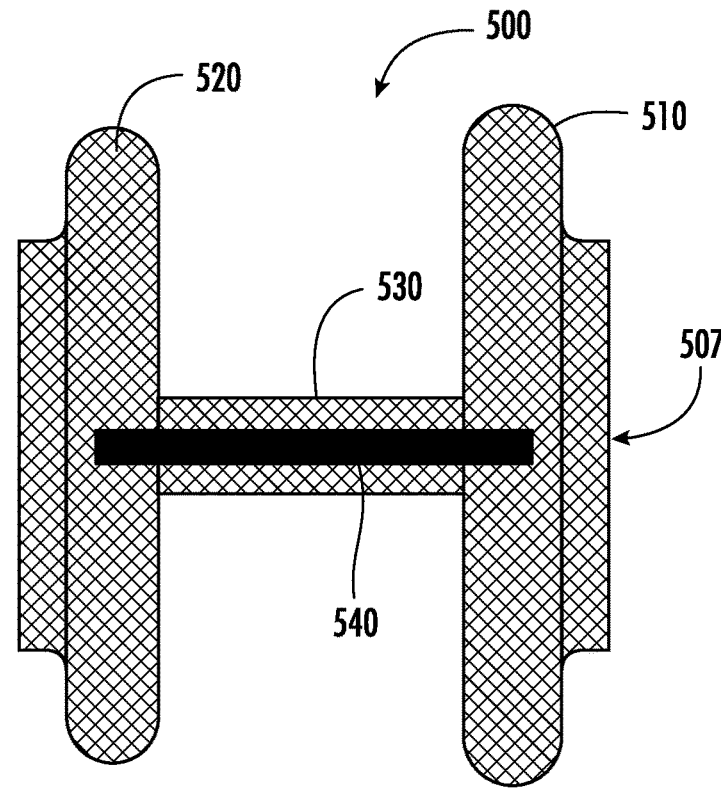

FIG. 5 illustrates a schematic elevational view of another example of an embodiment of an occlusion device formed in accordance with various principles of the present disclosure.

DETAILED DESCRIPTION

The following detailed description should be read with reference to the drawings, which depict illustrative embodiments. It is to be understood that the disclosure is not limited to the particular embodiments described, as such may vary. All apparatuses and systems and methods discussed herein are examples of apparatuses and/or systems and/or methods implemented in accordance with one or more principles of this disclosure. Each example of an embodiment is provided by way of explanation and is not the only way to implement these principles but are merely examples. Thus, references to elements or structures or features in the drawings must be appreciated as references to examples of embodiments of the disclosure, and should not be understood as limiting the disclosure to the specific elements, structures, or features illustrated. Other examples of manners of implementing the disclosed principles will occur to a person of ordinary skill in the art upon reading this disclosure. In fact, it will be apparent to those skilled in the art that various modifications and variations can be made in the present disclosure without departing from the scope or spirit of the present subject matter. For instance, features illustrated or described as part of one embodiment can be used with another embodiment to yield a still further embodiment. Thus, it is intended that the present subject matter covers such modifications and variations as come within the scope of the appended claims and their equivalents.

It will be appreciated that the present disclosure is set forth in various levels of detail in this application. In certain instances, details that are not necessary for one of ordinary skill in the art to understand the disclosure, or that render other details difficult to perceive may have been omitted. The terminology used herein is for the purpose of describing particular embodiments only, and is not intended to be limiting beyond the scope of the appended claims. Unless defined otherwise, technical terms used herein are to be understood as commonly understood by one of ordinary skill in the art to which the disclosure belongs. All of the devices and/or methods disclosed and claimed herein can be made and executed without undue experimentation in light of the present disclosure.

As used herein, "proximal" refers to the direction or location closest to the user (medical professional or clinician or technician or operator or physician, etc., such terms being used interchangeably herein without intent to limit, and including automated controller systems or otherwise), etc., such as when using a device (e.g., introducing the device into a patient, or during implantation, positioning, or delivery), and/or closest to a delivery device, and "distal" refers to the direction or location furthest from the user, such as when using the device (e.g., introducing the device into a patient, or during implantation, positioning, or delivery), and/or closest to a delivery device. "Longitudinal" means extending along the longer or larger dimension of an element. "Central" means at least generally bisecting a center point and/or generally equidistant from a periphery or boundary, and a "central axis" means, with respect to an opening, a line that at least generally bisects a center point of the opening, extending longitudinally along the length of the opening when the opening comprises, for example, a tubular element, a channel, a cavity, or a bore. As used herein, a passage or lumen is not limited to a circular cross-section. As used herein, a "free end" of an element is a terminal end at which such element does not extend beyond.

In accordance with various principles of the present disclosure, an implantable device is configured to occlude (understood herein to include fully or substantially fully or even partially occlude, unless otherwise indicated) flow of material through an anatomical deployment site. As used herein, a deployment site of a device is a site or location at which the device is deployed, positioned, implanted, extended, placed, etc. (such terms being used interchangeably herein without intent to limit) within a human body, and may also be the intended treatment site or position of the device once deployed and in use. The deployment site may be a body passage or lumen, such terms being used interchangeably herein without intent to limit, the broad principles of the present disclosure being applicable to various shapes and sizes of body passages, lumens, cavities, etc., or other anatomical structures. The body passage may extend between anatomical structures (e.g., a body cavity or organ adjacent the body passage) with a diameter generally larger than the body passage.

An occlusion device formed in accordance with various principles of the present disclosure may be deployed with a saddle region of the occlusion device extending across, through, within, etc. (such terms being used interchangeably herein without intent to limit) a body passage. The body passage may have an inlet and an outlet, and the implantable device may be provided with retention members (which may be alternatively referenced as flanges) seated with respect to an anatomical structure (e.g., a body wall) along or adjacent the inlet and/or outlet of the body passage as anti-migration structures configured to resist migration of the implantable device from the deployment site (e.g., with respect to the body passage). It will be appreciated that terms such as resist, inhibit, prevent (and other grammatical forms thereof) may be used interchangeably herein without intent to limit. The retention members may extend radially outward from along either end of intermediate region (along which the saddle is positioned). It will be appreciated that terms such as along or at or on or adjacent an end may be used interchangeably herein without intent to limit unless otherwise stated, and are intended to indicate a general relative spatial relation rather than a precisely limited location. The retention members are configured to engage one or more anatomical structures at the deployment site to inhibit movement of the occlusion device with respect to the deployment site. For instance, a retention member may be in the form of a lateral extension or flange wider than the intermediate region of the device and wider than a body passage in which the intermediate region of the device is deployed. The retention members are wider (in a radial direction transverse to the longitudinal axis of the body passage) than the saddle, and are configured to seat against a body wall extending radially outwardly from the body passage.

In some embodiments, at least one of the retention members is configured to resist migration of the implantable device with respect to the deployment site. In some embodiments, the first retention member and the second retention members are shaped similarly, such as with curved surfaces oriented to resist migration of the retention members, although such shapes may not have the same dimensions (i.e., the shapes may have different relative dimensions, scales, or proportions). For instance, the first retention member and the second retention member may be substantial duplicates of each other (optionally with different relative proportions), oriented in generally the same direction. Alternatively, in some embodiments, the first retention member and the second retention member may be mirror images (e.g., similar shapes facing in generally opposite directions, optionally with different relative proportions). In some embodiments, the first retention member and the second retention member are not generally the same or symmetrical. For instance, the first retention member and the second retention member may have different shapes, dimensions, relative proportions, etc. In some embodiments, a coating is applied to a portion of at least one of the retention members to strengthen and/or reduce flexibility of the retention member to increase the pull out strength thereof. In some embodiments, at least a portion of the surfaces of at least one of the retention member in contact with tissue at the deployment site are configured (e.g., not coated with a material which may inhibit tissue ingrowth) to promote tissue ingrowth with respect thereto. It will be appreciated that a coating may be applied to a surface of an outwardly facing side of a retention member, facing away from the saddle and not in contact with tissue, whereas at least a portion of surfaces of an inwardly-facing side of a retention member in contact with tissue are configured to promote tissue ingrowth with respect thereto. In some embodiments, at least one of the retention members is formed with a double wall (two walls adjacent and in contact or spaced apart from each other), each wall forming a side of the retention member. The wall of the double-wall retention member closer to the saddle (and generally contacting tissue at the deployment site) may be considered the inner side of the retention member, and the wall of the double-wall retention member further from the saddle (and generally not contacting tissue) may be referenced herein as the outer side of the retention member. In some embodiments, more than one retention member extends along one or both ends of the occlusion device.

In some embodiments, the first retention member and the second retention member are not generally the same or symmetrical. For instance, the first retention member and the second retention member may have different shapes, dimensions, relative proportions, etc. In some embodiments, an occlusion device positioned across a pylorus may have an enlarged gastric retention member (e.g., with a diameter larger than the duodenal retention member) to resist distal migration from the stomach into the duodenum. In some embodiments, an occlusion device positioned across a pylorus may have an elongated duodenal retention member, extending further from the saddle region than does the gastric retention member, to extend into the duodenum to enhance retention therein.

In accordance with an aspect of the present disclosure, the implantable device may be particularly configured to occlude flow of material through an anatomical structure. Such terms as occlude, block, prevent, inhibit, impede, reduce, delay, etc. (and various conjugations thereof) may be used interchangeably herein without intent to limit to indicate reduction of flow of materials by greater than 50%, and up to 100%, including increments of about 1% therebetween. In some deployment sites, complete occlusion may not be feasible because of various flow patterns through the passage or other anatomical features of the body passage. For instance, in embodiments in which the occlusion device is configured to be deployed across a pylorus, a considerable amount of fluid flow pressure may be imposed on the gastric side of the device, and/or a considerable amount of back pressure may be imposed on the duodenal side of the device. Accordingly, a small lumen may remain through the occlusion device, such as sufficient to allow passage of gases or low-viscosity fluids without causing excess pressure on the occlusion device which may dislodge the occlusion device.

In accordance with various principles of the present disclosure, an occlusion element configured to occlude at least a portion of the lumen defined through an occlusion device is positioned on to at least a portion of an intermediate region of the occlusion device in a manner to inhibit or prevent flow of material through the lumen therethrough. The occlusion element may be a separately formed element applied to the saddle (e.g., within the lumen through the saddle, and/or over at least a portion of the exterior of the saddle), or may be a further deformation of the saddle (e.g., a crimp). For the sake of convenience, and without intent to limit, reference is made herein to an occlusion element as applying to an occlusion element which is separately formed and applied to an exterior of the occlusion device and/or within the occlusion device as well as a further deformation of the saddle beyond the narrowing of an intermediate region to distinguish a saddle from retention members at the ends of the occlusion device.

In some embodiments, the occlusion element is a coating applied to at least a portion of the saddle of an occlusion device to form a plugging material. In some embodiments, the viscosity and/or percent solids of the coating material is selected to effect the desired occlusion. Additionally or alternatively, the thickness of the coating material applied to at least a portion of the saddle region to effect the desired occlusion. In some embodiments, the properties of the coating material (e.g., expandability, thickness, etc.) inhibits expansion of the saddle region of the occlusion device to inhibit or prevent flow of solid or semi-solid materials therethrough. In some embodiments, the coating material forms a plug occluding the passage through the occlusion device at least along a portion of an intermediate region of the occlusion device. Additionally or alternatively, the coating material may form a restraint with respect to the saddle which limits expansion of a region of a saddle of an expandable occlusion device, thereby occluding passage of materials through the lumen of the occlusion device. In some embodiments, the occlusion device is formed of a plurality of filaments or the like which are braided, woven, interwoven, knitted, wrapped, intertwined, looped, (e.g., bobbinet-style), knotted, or the like (such terms being used interchangeably herein without intent to limit), or of a laser-cut tube (which may in some instances be considered to form a plurality of struts), or otherwise formed to facilitate such ability to shift configurations. It will be appreciated that the term filaments is used for the sake of convenience, and may be used interchangeably herein with such terms as wires or strands or fibers or struts or the like without intent to limit. Such formation of the walls of a device may leave a plurality of openings therethrough, such as between the filaments. It will be appreciated that the term openings is used for the sake of convenience, and may be used interchangeably herein with such terms as spaces or interstices or the like without intent to limit. A coating may be applied to the device, such as to extend through interstices in the walls of the device, to prevent flow of material through such interstices and to form an occlusion element. Such coating may be similar to coatings known in the art for use with occlusion devices to occlude flow through the walls of the device and/or to inhibit tissue ingrowth into or with respect to the walls of the occlusion device. It will be appreciate that such coating is generally less viscous and/or has a lower percentage of solids and/or would be applied in a smaller amount than the material used to occlude flow of materials through the lumen of the occlusion device, such as by forming a plug therein, in accordance with various principles of the present disclosure.

In some embodiments, an additional structure to enhance occlusion of materials through the lumen of an occlusion device may be provided along at least a portion of the saddle region of the occlusion device, such as a crimp (e.g., deformation of, or addition of a constricting element about the saddle region), or an added occlusion element (e.g., dowel, pin, bar, mandrel, etc.) may be inserted into the lumen of the occlusion device. Such additional structure may occlude at least a portion of a narrowed intermediate region of the occlusion device.

To facilitate delivery and deployment and optional removal endoscopically or transluminally (or otherwise, without the need for open surgery), a device formed in accordance with various principles of the present disclosure may be configured to shift or move between a collapsed or compact delivery configuration and an expanded deployment configuration. The device may be formed of a biocompatible material (e.g., metal or polymer or alloy), such as a shape memory or heat-formable material (e.g., a nickel-titanium alloy such as Nitinol or a Cobalt-Chromium-Nickel-Molybdenum alloy such as Elgiloy®) which may be advantageously used to facilitate expansion of the device into a desired deployment configuration.

Various embodiments of occlusion devices formed in accordance with various principles of the present disclosure will now be described with reference to examples illustrated in the accompanying drawings. Reference in this specification to "one embodiment," "an embodiment," "some embodiments", "other embodiments", etc. indicates that one or more particular features, structures, and/or characteristics in accordance with principles of the present disclosure may be included in connection with the embodiment. However, such references do not necessarily mean that all embodiments include the particular features, structures, and/or characteristics, or that an embodiment includes all features, structures, and/or characteristics. Some embodiments may include one or more such features, structures, and/or characteristics, in various combinations thereof. Moreover, references to "one embodiment," "an embodiment," "some embodiments", "other embodiments", etc. in various places in the specification are not necessarily all referring to the same embodiment, nor are separate or alternative embodiments necessarily mutually exclusive of other embodiments. When particular features, structures, and/or characteristics are described in connection with one embodiment, it should be understood that such features, structures, and/or characteristics may also be used in connection with other embodiments whether or not explicitly described, unless clearly stated to the contrary. It should further be understood that such features, structures, and/or characteristics may be used or present singly or in various combinations with one another to create alternative embodiments which are considered part of the present disclosure, as it would be too cumbersome to describe all of the numerous possible combinations and subcombinations of features, structures, and/or characteristics. Moreover, various features, structures, and/or characteristics are described which may be exhibited by some embodiments and not by others. Similarly, various features, structures, and/or characteristics or requirements are described which may be features, structures, and/or characteristics or requirements for some embodiments but may not be features, structures, and/or characteristics or requirements for other embodiments. Therefore, the present disclosure is not limited to only the embodiments specifically described herein, and the examples of embodiments disclosed herein are not intended as limiting the broader aspects of the present disclosure.

It will be appreciated that common features in the various drawings are identified by common reference elements and, for the sake of brevity and convenience, and without intent to limit, the descriptions of the common features are generally not repeated. For purposes of clarity, not all components having the same reference number are numbered. It will be appreciated that, in the following description, elements or components similar among the various illustrated embodiments with reference numbers greater than 100 are generally designated with the same reference numbers increased by a multiple of 100 and redundant description is generally omitted for the sake of brevity. Moreover, certain features in one embodiment may be used across different embodiments and are not necessarily individually labeled or described in detail when appearing in different embodiments, reference being made to prior descriptions of similar elements.

Turning now to the drawings, an example of an implantable device 100, referenced herein as an occlusion device 100 for the sake of convenience and without intent to limit, and formed in accordance with various principles of the present disclosure is illustrated in FIG. 1. The illustrated occlusion device 100 has a proximal end 101, a distal end 103, and an intermediate region 105 therebetween. A proximal retention member 110 is provided along the proximal end 101 of the occlusion device 100, and a distal retention member 120 is provided along the distal end 103 of the occlusion device 100, with a saddle 130 extending between the proximal end 101 and the distal end 103 and along the intermediate region 105. The saddle 130 may be configured to be positioned through a body passage. The retention members 110, 120 are wider than the saddle 130, and are positioned against a respective body wall surrounding (e.g., extending outwardly from) a respective inlet and outlet of the body passage to prevent migration of the occlusion device 100 with respect to the body passage (distally/proximally or downstream/upstream of the typical direction of flow of materials through the body passage). In the illustrated example of an embodiment, the saddle 130 is positioned within a pylorus P, the proximal retention member 110 is positioned in the stomach S (such as against the antrum) and configured to inhibit distal migration of the occlusion device 100 into the duodenum D, and the distal retention member 120 is positioned in the duodenum D and configured to inhibit proximal migration of the occlusion device 100 into the stomach S.

An example of an embodiment of an occlusion device 200 formed in accordance with various principles of the present disclosure is illustrated in FIG. 2, has a first (e.g., proximal) retention member 214 along a first (e.g., proximal) end 201 thereof, and a second (e.g., distal) retention member 216 along a second (e.g., distal) end 203 thereof, and a saddle 230 along an intermediate region thereof narrowed so that the diameter of the occlusion device lumen 207 within such portion of the saddle 230 may be minimized to close to 0 (e.g., fully closed) to occlude the lumen 207 through the occlusion device 200. It will be appreciated that it may be desirable to allow a small amount of material, such as gases or liquids, to pass through the lumen 207 so that pressures against the occlusion device 200 (e.g., backpressure from the duodenum D or pressure from gastric materials in the stomach S) do not dislodge or cause migration of the occlusion device 200. For instance, the narrowest portion of the lumen 207 through the occlusion device 200 may have a diameter of about 0-2 mm, such as 1-1.5 mm, including increments of 0.01 mm therebetween. It will be appreciated that the inner diameter of the saddle 230 generally is not equal to zero, such that some movement of liquid or gases through the saddle 230 into the duodenum is acceptable.

The illustrated occlusion device 200 may be formed from a plurality of filaments, such as braided to form the tubular element. The material of the tubular element (e.g., the material of filaments braided or woven to form the tubular element) may be a shape-memory material, such as, without limitation, a nickel-titanium alloy (e.g., Nitinol) or a Cobalt-Chromium-Nickel-Molybdenum alloy (e.g., Elgiloy®). The configuration of the occlusion device 200 may be set by shaping the shape set tubular element such as by compressing or constraining or constricting or clamping or otherwise narrowing the intermediate region 205 (e.g., with a mold form, also known as a mid-form) to form the saddle 230, and optionally expanding the end regions to form the retention members 210, 220. In accordance with various principles of the present disclosure, the ends of a tubular element from which an occlusion device is formed may be held (e.g., locked against slippage or rotation) while tooling is used to form the shape of the occlusion device. Accordingly, as may be appreciated, formation of an occlusion device with at least a portion of a saddle being formed narrower than saddles of prior occlusion devices allows an occlusion device to be formed with tools similar to those currently used to form an occlusion device with a saddle without further manipulation of the tubular element to narrow the saddle, such as twisting. The material of the thus formed occlusion device 200 may be treated (e.g., heated) to set the formed tubular element into the desired shape in a manner known to those of ordinary skill in the art, the details of which do not form a part of the present disclosure.

In accordance with various principles of the present disclosure, at least a portion of the intermediate region 205 of the occlusion device 200 is further narrowed to reduce the portion of the occlusion device lumen 207 extending through such portion of the saddle 230 to occlude the flow of materials through such narrowed portion of the saddle 230 and the lumen 207 by application of an occlusion element 240 thereto.

In some embodiments, the portion of the lumen 207 extending through the further narrowed portion of the saddle

230 is further narrowed or occluded by the application of a coating material thereto to form an occlusion element 240. The occlusion element 240 formed by the coating material may plug or otherwise block a portion of the lumen 207 within the narrowed portion of the saddle 230. Additionally or alternatively, the coating material may resist expansion of the saddle 230 (e.g., bolster inherent resistance to expansion) thereby restricting passage of materials through the saddle 230. The coating material may be formed from a biocompatible polymeric material, such as silicone, urethane, polyurethane, urethane polyether block amides (PEBA), polyethylene, polyethylene terephthalate (PET), polyvinylidene difluoride (PVDF), polytetrafluoroethylene (PTFE), expanded polytetrafluoroethylene (ePTFE), polyester, polypropylene, polynapthalene, Chronoflex®, C-Flex® thermoplastic elastomer, Krator® SEBS and SBS polymers, or similar biocompatible polymeric formulations and/or copolymers thereof and/or combinations thereof.

The coating material may be applied in a manner to increase the bulk of the coating to an extent that the coating occludes the saddle 230 by plugging the saddle 230 and/or by preventing expansion of the saddle 230. For instance, the thickness of the coating on the wall of the saddle 230 may be at least about 100 μm and even as thick as about 500 μm, including increments of 1 μm therebetween. In some embodiments, whereas approximately 0.1 g of coating material may be applied to coat a prior art occlusion device (e.g., to prevent passage of material through the wall thereof), up to about 0.3 g or even up to about 0.4 g of coating material may be applied to an occlusion device 200 to form an occlusion element 240 in accordance with various principles of the present disclosure. In some embodiments, one or more material properties of the coating allow the coating to form an occlusion element 240 (e.g., a plug or other form of obstruction) rather than simply a coating (e.g., simply a covering layer). More particularly, in contrast with typical coating materials used on prior art stents (e.g., to inhibit tissue ingrowth, and/or to prevent passage of materials through the stent wall, and/or to impart structural rigidity/decrease flexibility, and/or to impart a degree of lubriciousness such as to facilitate movement with respect to tissue or to prevent abrasion of tissue), one or more properties of the coating material contribute to the occlusion created by the narrowing of the intermediate region 205 of the occlusion device 200. In some embodiments, the coating material has a viscosity higher than prior art coatings used for purposes as described above, so that instead of simply coating the wall of the occlusion device 200, the coating may also form a mass (e.g., a plug) within the portion of the occlusion device lumen 207 within the saddle 230 to occlude the saddle 230. The additional viscosity may also allow the coating to form an occlusion element 240 within or about the saddle 230 to restrict expansion of the saddle 230 and thereby to inhibit or prevent passage of materials therethrough. Additionally or alternatively, in some embodiments, the coating material is a higher solids percent material (has a higher percentage of solids) than prior art coating materials, so that the coating material of the present disclosure may form a mass within the portion of the occlusion device lumen 207 within the saddle 230 to occlude the saddle 230 and/or a restraining element with respect to the saddle 230 to restrict expansion of the saddle 230 and thereby to inhibit or prevent passage of materials therethrough. Additionally or alternatively, in some embodiments, the coating material may be applied to have a sufficient thickness to result in occlusion of at least a portion of the lumen 207 extending through the saddle 230 and/or to restrict expansion of the saddle 230 and thereby to inhibit or prevent passage of materials therethrough. For instance, whereas a typical coating for inhibiting tissue ingrowth, increasing lubricity, etc., may have a thickness greater of about 45-55 μm, a coating forming an occlusion element 240 in accordance with various principles of the present disclosure may have a thickness of about 100 μm or greater, and may even have a thickness of about 500 μm, including increments of 1 μm therebetween. Additionally or alternatively, in some embodiments, the coating material may have a durometer sufficient to cause occlusion of the saddle 230 and/or to restrict the saddle 230 from expanding (to resist expansion of the saddle 230) and thereby to prevent or inhibit passage of materials therethrough. For instance, increases in the durometer affects the percent solids of the material, and the higher the percent solids, the less the material will flow during curing, resulting in a thicker layer of coating being applied Additionally or alternatively, in some embodiments, the flexibility and/or elasticity of the coating material may be selected to result in occlusion of at least a portion of the lumen 207 extending through the saddle 230 and/or to restrict expansion of the saddle 230 and thereby to inhibit or prevent passage of materials therethrough. For instance, the saddle 230 may be coated in such a fashion to prevent a lumen expansion of greater than about 2-5 mm and/or to allow no more than a 75% increase in the saddle outer diameter. It will be appreciated that one or more such properties, and/or other properties not listed herein, of the coating material may contribute to the coating material's ability to occlude (e.g., plug) and/or restrain the saddle 230, such as by being integrated into the saddle 230 or simply by being formed about the periphery of the saddle 230 to resist expansion of the saddle 230. As noted above, in some embodiments it may be desired to leave a lumen with a small diameter (e.g., 0.1-0.6 mm). In such embodiments, a very narrow mandrel or guidewire may be inserted through the lumen 207 of the occlusion device 200 before the coating is applied to a portion of the saddle 230 to leave a minimal inner diameter through a portion of the saddle 230 such as described above.

In some embodiments, the additional narrowing of the saddle 230 along with the coating material may achieve the desired occlusion without other mechanical deformation or other manipulation of the saddle 230, such as twisting the saddle 230. Generally, the occlusion device 200 is constrained or otherwise placed in a reduced-diameter configuration to allow for transluminal delivery through the body (e.g., for transcatheter delivery without invasive open surgery). Once the occlusion device 200 is deployed, the occlusion device 200 may shift from a delivery configuration (constricted, collapsed, reduced-diameter, etc. configuration) to a deployment (expanded) configuration with the occluded portion of the saddle 230 generally remaining in an occlusion configuration. For instance, upon deployment of the occlusion device 200, the coated portion of the saddle 230 may not shift into a configuration significantly different from its delivery configuration. For instance, the inner diameter of the saddle 230 may expand no more than about 2-5 mm and/or the outer diameter of the saddle 230 would not increase by more than about 75%.

In accordance with various principles of the present disclosure, the inner diameter of the portion of the lumen 207 within the further narrowed portion of the saddle 230 (formed to be narrower than typical saddles of prior art occlusion devices) may be 6 mm or less, and preferably less than about 5 mm or less, and even as small as about 2 mm, or as small as about 1.5 mm, or even as small as about 1 mm±0.2 mm, such measurements encompassing increments of about 0.1 mm therebetween. The outer diameter of such portion of the saddle 230 may be less about 7 mm or less, and preferably less than about 6 mm or less, and as small as about 2 mm, and even as small as about 2 mm±0.2 mm, such measurements encompassing increments of about 0.1 mm therebetween. The diameter of a filament (e.g., a wire) forming the occlusion device 200 may be about 0.005″ (0.127 mm) and even up to about 0.010″ (0.254 mm). It will be appreciated that "occlusion" of a portion of the lumen 207 through the saddle 230, as described herein, need not be complete occlusion, but may allow for passage of some fluids (gases and/or liquids) which otherwise may induce enough pressure on the occlusion device 200 to cause migration of the occlusion device 200 or otherwise to dislodge the occlusion device 100 from its deployment site, such as by allowing a lumen with a minimal diameter to extend through the occlusion device 200 as described above. For instance, the occlusion element 240 formed by the coating material may leave a portion of the lumen 207 through the saddle 230 with an inner diameter of less than about 2 mm but greater than 0, encompassing increments of about 0.1 mm therebetween.

A coating material used in accordance with various principles of the present disclosure to form an occlusion element 240 generally inhibits tissue ingrowth into the underlying structure. It will be appreciated that the coating material forming the occlusion element 240 need not be applied along the entire length of the saddle 230 along the longitudinal axis LA of the occlusion device 200 so that at least some tissue ingrowth is permitted (and possibly promoted) along the length of the saddle 230 without such coating material. It is believed that tissue ingrowth with respect to the occlusion device 200 enhances retention of the occlusion device 200 with respect to the body passage through which the occlusion device 200 is deployed, reducing and potentially preventing migration of the occlusion device 200 from its deployment site. The coating material may be limited to being applied only a few millimeters along the length of the saddle 230. For instance, in some embodiments, the saddle 230 of an occlusion device 200 configured to be positioned across a pylorus P may be sized to correspond to an average length of a pylorus P, approximately 17 mm long. In accordance with various principles of the present disclosure, coating material may be applied only about 2-3 mm along the length of the saddle 230. In some embodiments, the coating material is limited to a generally central position along the length of the saddle 230.

To further enhance the benefits of tissue ingrowth with respect to the occlusion device 200, the inwardly-facing sides 212, 222, of the retention members 210, 220, respectively, are configured (e.g., uncoated) to promote tissue ingrowth. In the example of an embodiment of an occlusion device 200 illustrated in FIG. 2, the retention members 210, are double-wall retention members such that the inwardly-facing sides 212, 222 of the retention members 210, 220 are inner walls of the double-wall retention members 210, 220, and the outwardly-facing sides 214, 224 of the retention members 210, 220 are outer walls of the double-wall retention members 210, 220. The retention members 210, 220 generally are positioned against tissue surrounding the inlet/outlet of the passage in which the occlusion device 200 is deployed (e.g., against the stomach S and the duodenum D) and may have diameters significantly larger than the diameter of the saddle 230 to increase the surface area of the occlusion device 200 contacting tissue. For instance, the outer diameter of one or both of the retention members 210, 220 may be at least about 10 times larger than the outer diameter of the saddle 230, and even up to about 20 times larger than the outer diameter of the saddle 230, including all multiples therebetween. Such increase in surface area of the sides of the retention members 210, 220 contacting tissue at the deployment site not only increases the pullout strength of the retention members 210, 220 (resistance to migration with respect to the deployment site), but also provides greater surface area for tissue ingrowth to increase the anti-migration effect of tissue ingrowth into the occlusion device 200. In some embodiments, the outer diameter of the retention members 210, 220 is at least about 30 mm or larger, and may be as large as about 50 mm or even larger, such measurements encompassing increments of about 0.5 mm therebetween. The retention members 210, 220 may be formed from a tubular element, such as a braided tubular element, forming the occlusion device 200 as a result of constricting the intermediate region 205 to form the saddle 230 and/or by expanding the end regions of the tubular element (e.g., by inserting a washer therein) to form the retention members 210, 220. In some embodiments, end rings are used to form extensions or lips 216, 226 axially extending from the retention members 210, 220 in a direction away from the saddle 230.

In some embodiments, a coating may be applied to portions of the occlusion device 200 which do not contact tissue to impart structural rigidity for anti-migration purposes as known in the art. The coating may include any suitable biocompatible material known or heretofore known in the art for such purposes, such as a polymeric material, such as silicone, urethane, polyurethane, urethane polyether block amides (PEBA), polyethylene terephthalate (PET), polyvinylidene difluoride (PVDF), polytetrafluorethylene (PTFE), expanded polytetrafluoroethylene (ePTFE), polyester, polypropylene, polynapthalene, Chronoflex®, C-Flex® thermoplastic elastomer, Krator® SEBS and SBS polymers, etc., or similar biocompatible polymeric formulations and/or copolymers thereof and/or combinations thereof. The coating may be applied to at least a portion of the outer faces 214, 224 of the retention members 210, 220 and/or the welds (along ends 201, 203 of the occlusion device 200, which may be welded if the occlusion device 200 is formed of a braided or woven material) or lips 216, 226 (axial extensions of the occlusion device 200 outwardly from the outwardly-facing sides of retention members 210, 220 in a direction away from the saddle 230).

In some embodiments, the occlusion device may be configured to have a more gradual transition from the narrow saddle to the wider retention members illustrated in FIG. 2. For instance, in the example of an embodiment of an occlusion device 300 illustrated in FIG. 3, the diameter of the saddle 330 transitions to the wider retention members 310, 320 with a gradual increase in the outer diameter of the saddle 330. For instance, the diameter of the saddle 330 may transition to the wider retention members 310, at an approximately 35-40° slope. A transition region T, such as illustrated in FIG. 3, may be configured to allow the saddle 330 to match the contours of the anatomy of the deployment site better to increase contact of the saddle 330 with tissue and/or to increase the surface area of the saddle 330 and thereby to improve tissue ingrowth in an uncoated saddle 330. A forming tool with a radiused surface may be used to form a saddle 330 such as illustrated in FIG. 3 to reduce fatigue of the material with which the occlusion device 300 is formed. In some embodiments, an occlusion element 340, such as the occlusion element 240 of the occlusion device 200 described above and illustrated in FIG. 2, is provided in the central region C and does not extend into the transition region T. In some embodiments, the central region C may have a short length relative to the transition region T, and the transition region T may be characterized by a greater increase in outer diameter per millimeter than any changes in outer diameter along the central region C. For instance, in some embodiments, the transition region T may have a length of about 16-18 mm±1 mm (and including increments of 0.05 mm therebetween), and the central region C may have a length of about 4-8 mm±1 mm (and including increments of 0.05 mm therebetween). In some embodiments, the transition region T remains uncoated.

As noted above, the occlusion element may be formed in a variety of manners to achieve the desired occlusion through at least a narrowed portion of a saddle of an occlusion device formed in accordance with various principles of the present disclosure. An example of a crimp-type occlusion element 440 is illustrated in FIG. 4 over a saddle 430 of the illustrated example of an embodiment of an occlusion device 400. The occlusion element 440 may be a swaged formation, or a separately formed clamp or band applied over the exterior of the saddle 430. The occlusion element 440 is formed to inhibit expansion of the saddle 430 to occlude passage of materials through at least the portion of the occlusion device lumen 407 extending through the saddle 430. An example of a separately formed occlusion element 540, such as a dowel, pin, bar, rod, mandrel, or the like, is illustrated in FIG. 5 within the saddle 530 of the illustrated example of an embodiment of an occlusion device 500 to occlude flow of materials through the saddle 530. Such occlusion elements as illustrated in FIGS. 4 and 5, as well as the occlusion elements 240, 340 illustrated in FIGS. 2 and 3, and described above, allow for an occlusion device to have an uncoated saddle promoting tissue ingrowth therein while also occluding flow of materials therethrough.

In view of occlusion devices formed in accordance with various principles of the present disclosure having narrower saddles with lumens which are substantially or close to occluded at least along a portion (e.g., a central region) thereof, typical delivery systems may need to be modified. For instance, various implantable devices with lumens therethrough (e.g., stents and prior occlusion devices) may be delivered over a flexible tubular elongate member (which may, in turn, be navigated through a delivery sheath and/or an endoscope and/or a delivery catheter) of a delivery/deployment system. A guidewire may be initially inserted into the body transluminally to guide the delivery/deployment device to the deployment site to deploy the implantable device at the desired location at the deployment site. The lumen of the implantable device, and the flexible tubular elongate member over which the implantable device is delivered, may be threaded over the guidewire to be guided by the guidewire. An occlusion device formed in accordance with various principles of the present disclosure may not have a sufficiently large lumen therethrough (at least not at the occluded portion) to allow a flexible tubular elongate member to be inserted therein. Accordingly, an occlusion device formed in accordance with various principles of the present disclosure may be inserted directly over the guidewire to be guided to the desired location at the deployment site. A pusher such as known by those of ordinary skill in the art may be used to push the occlusion device out of a delivery sheath in which it is transluminally delivered through the body to the deployment site. It will be appreciated that various aspects of the above disclosure may be applied in other passages within the body to reduce flow through such passage. Although embodiments of the present disclosure may be described with specific reference to medical devices and systems and procedures for treating the gastrointestinal system, it should be appreciated that such medical devices and methods may be used to treat tissues of the abdominal cavity, digestive system, urinary tract, reproductive tract, respiratory system, cardiovascular system, circulatory system, and the like.

The foregoing discussion has broad application and has been presented for purposes of illustration and description and is not intended to limit the disclosure to the form or forms disclosed herein. It will be understood that various additions, modifications, and substitutions may be made to embodiments disclosed herein without departing from the concept, spirit, and scope of the present disclosure. In particular, it will be clear to those skilled in the art that principles of the present disclosure may be embodied in other forms, structures, arrangements, proportions, and with other elements, materials, and components, without departing from the concept, spirit, or scope, or characteristics thereof. For example, various features of the disclosure are grouped together in one or more aspects, embodiments, or configurations for the purpose of streamlining the disclosure. However, it should be understood that various features of the certain aspects, embodiments, or configurations of the disclosure may be combined in alternate aspects, embodiments, or configurations. While the disclosure is presented in terms of embodiments, it should be appreciated that the various separate features of the present subject matter need not all be present in order to achieve at least some of the desired characteristics and/or benefits of the present subject matter or such individual features. One skilled in the art will appreciate that the disclosure may be used with many modifications or modifications of structure, arrangement, proportions, materials, components, and otherwise, used in the practice of the disclosure, which are particularly adapted to specific environments and operative requirements without departing from the principles or spirit or scope of the present disclosure. For example, elements shown as integrally formed may be constructed of multiple parts or elements shown as multiple parts may be integrally formed, the operation of elements may be reversed or otherwise varied, the size or dimensions of the elements may be varied. Similarly, while operations or actions or procedures are described in a particular order, this should not be understood as requiring such particular order, or that all operations or actions or procedures are to be performed, to achieve desirable results. Additionally, other implementations are within the scope of the following claims. In some cases, the actions recited in the claims can be performed in a different order and still achieve desirable results. The presently disclosed embodiments are therefore to be considered in all respects as illustrative and not restrictive, the scope of the claimed subject matter being indicated by the appended claims, and not limited to the foregoing description or particular embodiments or arrangements described or illustrated herein. In view of the foregoing, individual features of any embodiment may be used and can be claimed separately or in combination with features of that embodiment or any other embodiment, the scope of the subject matter being indicated by the appended claims, and not limited to the foregoing description.

In the foregoing description and the following claims, the following will be appreciated. The phrases "at least one", "one or more", and "and/or", as used herein, are open-ended expressions that are both conjunctive and disjunctive in operation. The terms "a", "an", "the", "first", "second", etc., do not preclude a plurality. For example, the term "a" or "an" entity, as used herein, refers to one or more of that entity. As such, the terms "a" (or "an"), "one or more" and "at least one" can be used interchangeably herein. All directional references (e.g., proximal, distal, upper, lower, upward, downward, left, right, lateral, longitudinal, front, back, top, bottom, above, below, vertical, horizontal, radial, axial, clockwise, counterclockwise, and/or the like) are only used for identification purposes to aid the reader's understanding of the present disclosure, and/or serve to distinguish regions of the associated elements from one another, and do not limit the associated element, particularly as to the position, orientation, or use of this disclosure. Connection references (e.g., attached, coupled, connected, and joined) are to be construed broadly and may include intermediate members between a collection of elements and relative movement between elements unless otherwise indicated. As such, connection references do not necessarily infer that two elements are directly connected and in fixed relation to each other. Identification references (e.g., primary, secondary, first, second, third, fourth, etc.) are not intended to connote importance or priority, but are used to distinguish one feature from another.

The following claims are hereby incorporated into this Detailed Description by this reference, with each claim standing on its own as a separate embodiment of the present disclosure. In the claims, the term "comprises/comprising" does not exclude the presence of other elements, components, features, regions, integers, steps, operations, etc. Additionally, although individual features may be included in different claims, these may possibly advantageously be combined, and the inclusion in different claims does not imply that a combination of features is not feasible and/or advantageous. In addition, singular references do not exclude a plurality. Reference signs in the claims are provided merely as a clarifying example and shall not be construed as limiting the scope of the claims in any way.

What is claimed is:

1. An occlusion device having a first end, a second end, and an intermediate region therebetween, and defining a lumen therethrough, said occlusion device comprising:
   a radially outwardly extending first retention member along the first end of said occlusion device;
   a radially outwardly extending second retention member along the second end of said occlusion device;
   a saddle along the intermediate region of said occlusion device and defining a lumen therethrough; and
   an occlusion element positioned within the lumen of said saddle to partially occlude flow of materials through the lumen of said saddle;
   wherein said occlusion element is formed of a coating material filling the lumen of said saddle to partially occlude flow of material through the lumen of the saddle.

2. The occlusion device of claim 1, wherein at least one of the viscosity, solids percent, thickness, durometer, or flexibility of said coating material is selected to allow said coating material to form a plug occluding at least a portion of the lumen through said occlusion device.

3. The occlusion device of claim 2, wherein said coating material fills the portion of the lumen to define an inner diameter of less than 2 mm through said portion of the lumen.

4. The occlusion device of claim 2, wherein said coating material extends only about 2-3 mm along said saddle.

5. The occlusion device of claim 2, wherein said coating material is limited to a central region of said saddle with surrounding regions of said saddle uncoated to promote tissue ingrowth.

6. The occlusion device of claim 1, wherein at least one of the viscosity, solids percent, thickness, durometer, or flexibility of said coating material is selected to allow said coating material to restrain at least a portion of said saddle from expanding, thereby occluding flow of material through the lumen defined through said occlusion device.

7. The occlusion device of claim 1, wherein the outer diameter of at least one of said first retention member or said second retention member is at least about-ten times greater than an outer diameter of said saddle.

8. The occlusion device of claim 1, wherein said first retention member and said second retention member have surfaces facing said saddle which are configured to promote tissue ingrowth therein.

9. A method of occluding flow of materials through an occlusion device, said method comprising:

narrowing an intermediate region of a tubular element to define a saddle with a lumen therethrough;

forming a first retention member with an outer diameter larger than the outer diameter of the saddle along a first end of the tubular element;

forming a second retention member with an outer diameter larger than the outer diameter of the saddle along a second end of the tubular element; and applying a coating material within a portion of the lumen through the saddle to partially occlude the portion of the lumen through the saddle to partially occlude flow of material through the lumen through the saddle.

10. The method of claim 9, further comprising constraining a portion of the saddle so that the diameter of the lumen within the constrained portion of the saddle is 6 mm or less.

11. The method of claim 9, wherein applying a coating further comprises applying a coating material with at least one of a viscosity, solids percent, thickness, durometer, or flexibility allowing the coating material to form a plug occluding at least a portion of the lumen through the occlusion device and/or to restrain the coated portion of the saddle from expanding to thereby partially occlude flow of material through the lumen defined through said occlusion device.

12. The method of claim 9, further comprising leaving a portion of the saddle, and the surfaces of the first retention member and the second retention member facing the saddle configured to promote tissue ingrowth therein.

13. An occlusion device having a first end, a second end, and an intermediate region therebetween, and defining a lumen therethrough, said occlusion device comprising:

a radially outwardly extending first retention member along the first end of said occlusion device;

a radially outwardly extending second retention member along the second end of said occlusion device;

a saddle along the intermediate region of said occlusion device and defining a lumen therethrough; and an occlusion element positioned within the lumen of said saddle to partially occlude flow of materials through the lumen of said saddle;

wherein at least a portion of the lumen remains in a partially occluded configuration during use of said occlusion device.

14. The occlusion device of claim 13, wherein said occlusion element is formed from a coating material applied to said saddle.

15. The occlusion device of claim 13, wherein said occlusion element is positioned about a portion of the exterior of said saddle to restrict expansion of said saddle.

16. The occlusion device of claim 14, wherein said occlusion element extends within a portion of the lumen extending through said saddle to form a plug within a portion of the lumen extending through said saddle.

17. The occlusion device of claim 14, wherein said coating material is limited to a central region of said saddle with surrounding regions of said saddle uncoated to promote tissue ingrowth.

18. The occlusion device of claim 17, wherein surfaces of the first retention member and the second retention member facing the saddle uncoated to promote tissue ingrowth therein.

19. The occlusion device of claim 13, wherein the outer diameter of at least one of said first retention member or said second retention member is at least ten times greater than an outer diameter of said saddle.

20. The occlusion device of claim 13, wherein the diameter of at least a portion of the lumen extending through said saddle is less than about 6 mm.

* * * * *